United States Patent [19]

Hayashi et al.

[11] Patent Number: 4,764,970
[45] Date of Patent: Aug. 16, 1988

[54] METHOD AND APPARATUS FOR DETECTING CRACKS

[75] Inventors: Makoto Hayashi; Masahiro Otaka; Tasuku Shimizu, all of Hitachi; Shinji Sakata, Kathuta, all of Japan

[73] Assignee: Hitachi, Ltd., Tokyo, Japan

[21] Appl. No.: 852,313

[22] Filed: Apr. 15, 1986

[30] Foreign Application Priority Data

Apr. 15, 1985 [JP] Japan ................. 60-78304
Apr. 17, 1985 [JP] Japan ................. 60-80104

[51] Int. Cl.⁴ ............................................. G06K 9/00
[52] U.S. Cl. ........................................ 382/8; 324/64;
324/158 P; 358/101; 358/106; 358/107;
364/507; 382/1
[58] Field of Search ............... 324/64, 158 P, 357;
382/1, 8, 28; 364/507, 551, 552; 358/101, 106, 107

[56] References Cited

U.S. PATENT DOCUMENTS

| | | | |
|---|---|---|---|
| 3,699,436 | 10/1972 | Shigematsu et al. | 324/64 |
| 3,735,253 | 5/1973 | Seger | 324/64 |
| 4,267,506 | 5/1981 | Shiell | 324/158 P |
| 4,353,255 | 10/1982 | Fukuda et al. | 364/507 |
| 4,368,422 | 1/1983 | Bachet et al. | 324/64 |
| 4,656,595 | 4/1987 | Hognestad | 324/64 |
| 4,683,419 | 7/1987 | Nevelmann et al. | 324/64 |
| 4,703,252 | 10/1987 | Perloff et al. | 324/158 P |

OTHER PUBLICATIONS

Baudin et al, "A Pulsed d.c. P.D. Technique-Applications to Three-Dimensional Crack Fronts", pp. 159–174.

Primary Examiner—Leo H. Boudreau
Assistant Examiner—Jose L. Couso
Attorney, Agent, or Firm—Antonelli, Terry & Wands

[57] ABSTRACT

The invention scans potential measurement terminals on the surface of a structural member to measure a potential distribution on the surface, detects the direction of a crack from the potential distribution and determining a detailed potential distribution in the direction of the crack thus detected. This potential distribution is compared with master curves of the potential distributions of cracks of various shapes, that have been obtained by analysis in advance, in order to detect the shape of the crack. The present invention can detect accurately a crack shape.

3 Claims, 18 Drawing Sheets

2C =17mm

2C = 17mm

METHOD AND APPARATUS FOR DETECTING CRACKS

BACKGROUND OF THE INVENTION

1. Field of the Invention

This invention relates generally to a method and apparatus for detecting cracks on the surface of structural members of nuclear power equipment, steam turbines, hydraulic turbines, and the like, and more particularly to a method and apparatus for detecting highly accurately the shapes of cracks which is indispensable for understanding the development state of cracks.

2. Description of the Prior Art

A method of measuring the development state of cracks by causing a current to flow around a crack and measuring a voltage across the crack is disclosed in the article "ADVANCES IN CRACK LENGTH MEASUREMENT" (editor: C. J. Beevers) in ENGINEERING MATERIALS ADVISORY SERVICES LTD., (1982). In accordance with this prior art method, however, current supply terminals and voltage measurement terminals are fixed. Therefore, when the positions of of cracks are limited to particular positions, the method can grasp the development state of the cracks, but if the crack positions are not at the center of the voltage measurement terminals, the detection accuracy of the crack depth drops and detection of the crack shape is extremely difficult.

OBJECT OF THE INVENTION

It is therefore an object of the present invention to provide a method and apparatus which can detect highly accurately the shapes of surface cracks developing on structural members.

SUMMARY OF THE INVENTION

The present invention relates to a method and apparatus for detecting the occurrence positions and shapes of cracks on the surface of structural members using applying a d.c. current to their surface by pairs of power feed terminals and measuring the positions of and shapes of the surface cracks using a pair of voltage measurement terminals positioned between the power feed terminals. The voltage measurement terminals are scanned on the surface of the structural member to measure the potential distribution on the surface, from which the direction of the crack is detected. Next, detailed potential distribution is determined in the direction of the detected crack, which is then compared with a master curve of potential distributions for various shapes of cracks, that has in advance been analyzed and prepared in advance, so as to determine the shape of the cracks. Thus, the present invention can highly accurately detect the shapes of cracks which is indispensable for understanding the development state of cracks.

DESCRIPTION OF THE PREFERRED EMBODIMENTS

Hereinafter, one embodiment of the present invention will be described with reference to the accompanying drawings.

Figure 1:
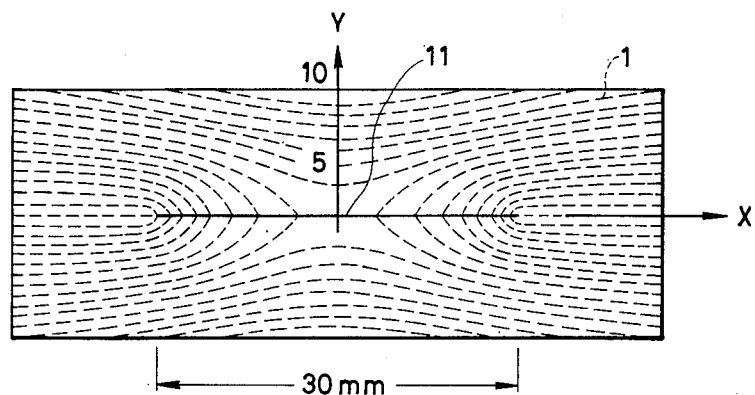
FIG. 1 is a potential distribution diagram around a crack which is determined by the analysis of a finite element method in a crack shape detection method in accordance with the present invention.

FIG. 1 is an equipotential diagram showing potential distribution in the proximity of a surface crack. This is the result obtained by analysis in accordance with a finite element method when a semicircular crack which is 30 mm long and 15 mm deep exists on a 20 mm-thick flat plate. Even when the material varies, only the absolute value of the potential changes but the distribution shape remains unchanged. Consider the potential distribution on the crack surface; the equipotential lines creep below the crack surface. The number of equipotential lines that creep below the crack surface changes in accordance with the crack depth. It can be understood also that the potential distribution exhibits such distribution that is symmetric with the crack surface. In other words, since the potentials exhibit opposite distributions while interposing the crack between them, the crack position can be determined easily. Needless to say, when the potential difference between the positions that interpose the crack between them is measured, the potential difference can be detected because it becomes great at the position at which the crack exists.

Figure 2:
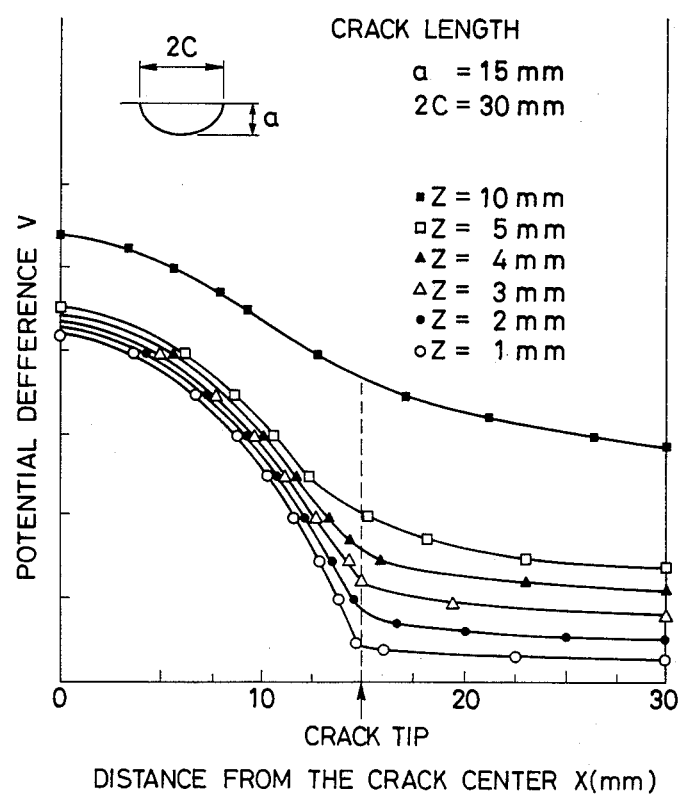
FIG. 2 is a potential distribution diagram of the potential distribution shown in FIG. 1 in the proximity of the crack in a direction parallel with the crack.

Next, FIG. 2 shows the calculation result of the potential distribution near the crack. The calculation is made for the crack shown in FIG. 1, and the diagram shows the potential distribution in the direction of an X axis at positions that are spaced apart by 1, 2, 3, 4, 5 and 10 mm from the crack in the direction of a Y axis, respectively. As can be seen clearly from this diagram, the crack shape can be judged to some extents even at the position spaced apart by 10 mm from the crack. However, it is difficult to detect highly accurately the crack shape at remote positions because the potential drops gradually. It is particularly difficult to specify the tip of the surface crack.

When the measuring position comes closer to the crack, however, the tip of the surface crack can be determined easily because peculiar points appear in the potential distribution at the tip of the surface crack. In addition, the potential is proportional to the crack depth. Therefore, the crack shape can be determined by measuring the potential distribution from the forward portion of the crack tip in the proximity of the pole of the crack along the crack, or measuring the potential difference across the crack.

Figure 3:
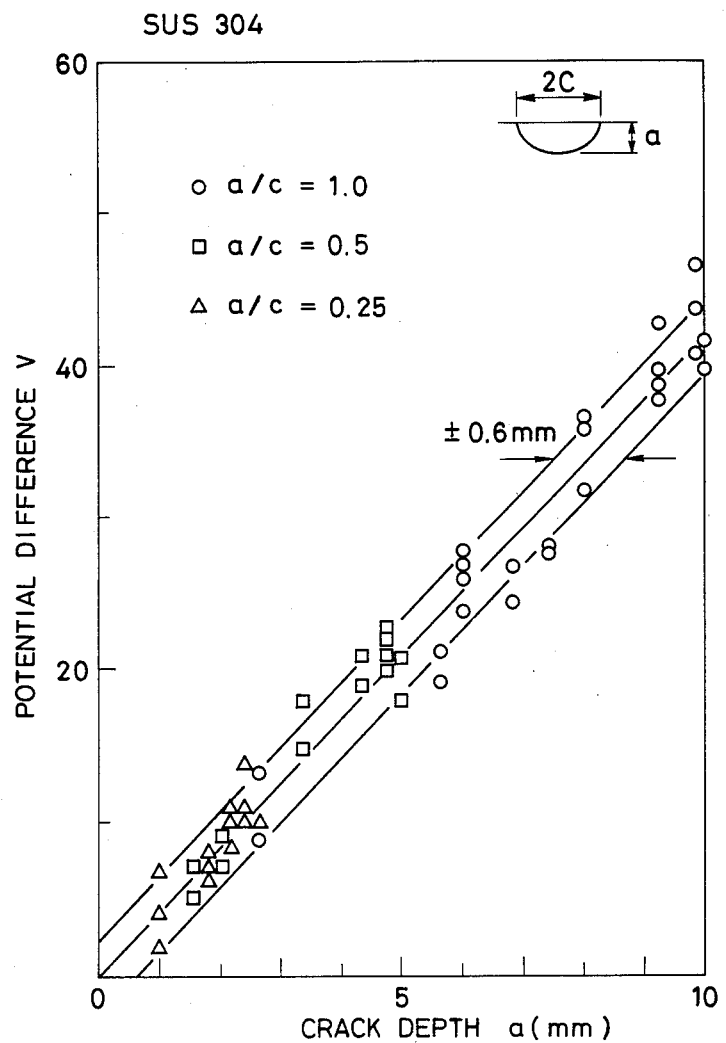
FIG. 3 is a diagram showing the relation between potential differences at each measurement position and crack depth obtained using stainless steel as a specimen.

FIG. 3 shows the relation between the potential difference and the crack depth whereby the potential difference is measured at a position spaced apart by 1 mm from the crack on a flat plate made of SUS 304 on which the crack is simulatedly formed by discharge work. The aspect ratios of the crack, i.e., a/c (a: crack depth and c: crack length) are 1.0, 0.5 and 0.25. The potential difference is proportional to the crack depth irrelevantly to the aspect ratio, though some variances exist. Therefore, the crack shape can be detected more accurately by measuring the potential distribution near the crack.

Figure 4:
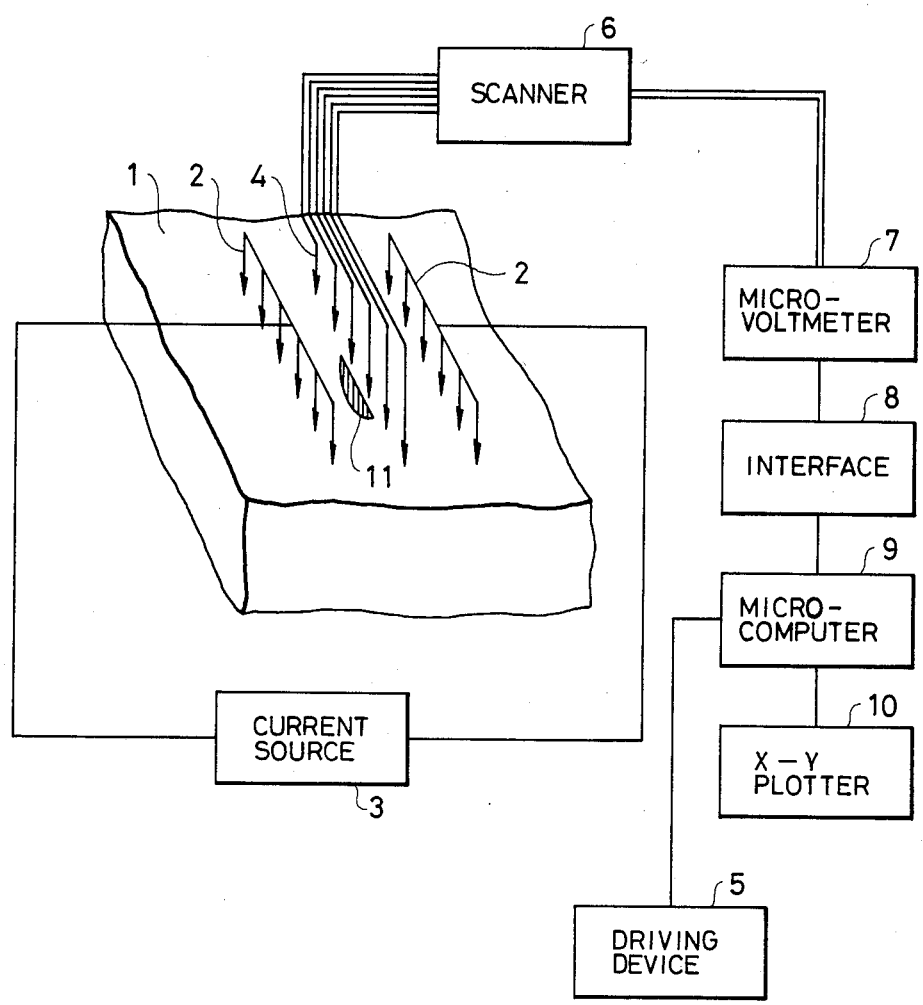
FIG. 4 is a perspective view showing the appearance of a crack shape detection apparatus in accordance with one embodiment of the present invention.

FIG. 4 is a schematic view of a detection apparatus for detecting the shape of the surface crack of a structural member. A d.c. current is applied to the structural member 1 having the surface crack 11 through a plurality of power feed terminal pairs 2 from a d.c. constant current source 3. A plurality of measurement terminals 4 are aligned at the center of the power feed terminal pairs 2 in parallel therewith. The power feed terminal pairs 2 and the measurement terminals 4 are fitted to a non-conductor substrate (not shown in the drawing) and the substrate is fitted to a driving device 5. The detection apparatus includes also a scanning mechanism. The potential difference between the measurement terminals 4 is measured by a micro-voltmeter 7 through a scanner 6. The output of this micro-voltmeter 7 is applied to a microcomputer 9 through an interface 8. The input potential difference is compared with a master curve stored in advance in the micro-computer 9 and calculated to determine the crack shape. The result of calculation of the crack shape is displayed by an X-Y plotter 10. Location of a flaw detection head (see FIG. 5) as the substrate, having the power feed terminal pairs 2 and the measurement terminals 4 fitted thereto, is made by the driving device 5, and the driving device 5 is in turn controlled by the micro-computer 9.

Figure 5:
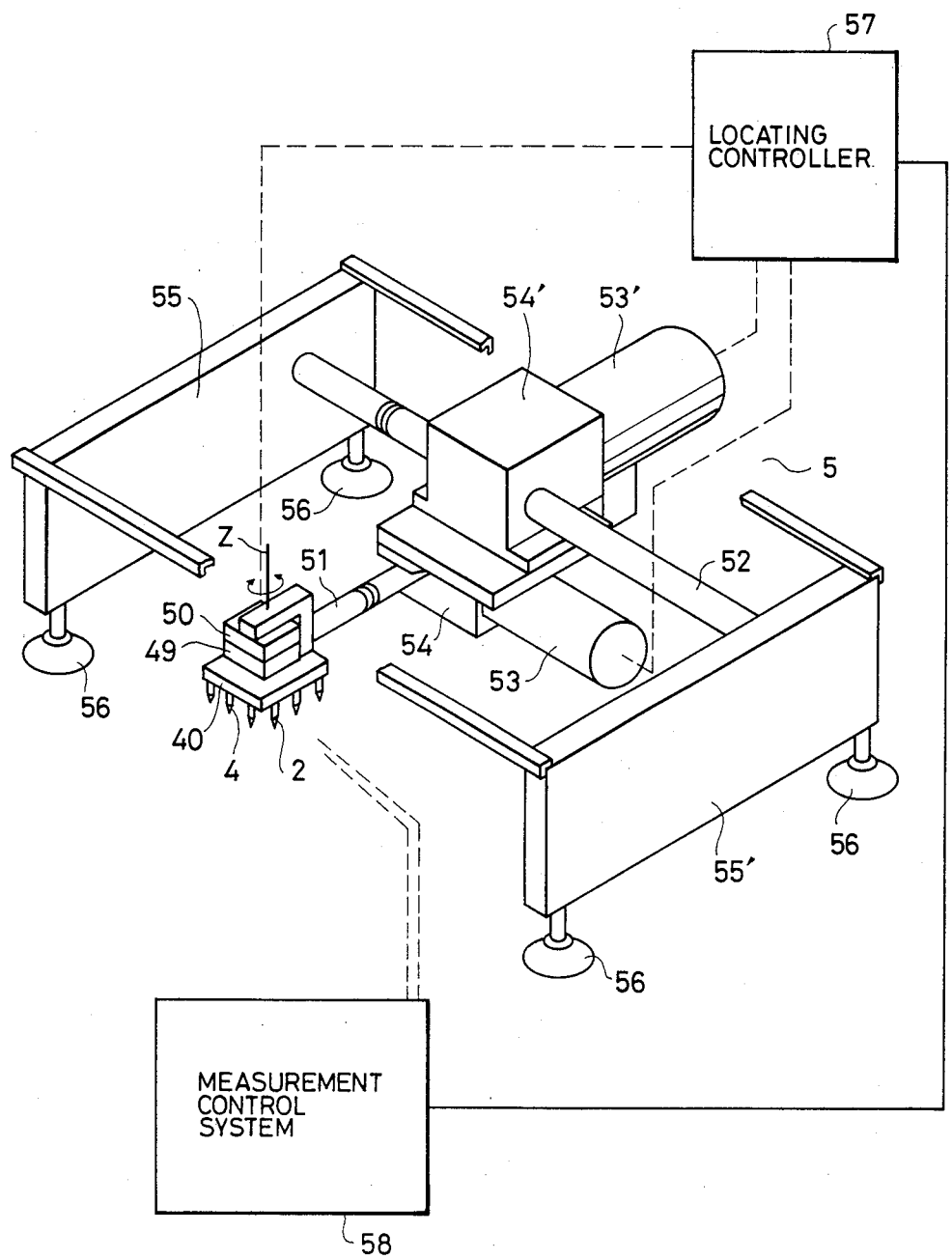
FIG. 5 is a detailed view of the crack shape detection apparatus.

FIG. 5 is a detailed view of the driving device 5 of the crack shape detection apparatus. The driving device 5 can rotate the flaw detection head 40 having the measurement terminals 4 and the power feed terminal pairs 2 around a Z axis by means of a stepping motor 50, and is equipped with an air cylinder 49 for pressing the measurement terminals 4 and the power feed terminal pairs 2 to the surface of the structural member. Furthermore, the driving device 5 has X- and Y-axes driving mechanisms 51 and 52 for moving the flaw detection head 40 on a two-dimensional plane, and each of the coordinates axes is driven by a motor 53, 53' and a reduction gear 54, 54'. The Y axis 52 is fixed to side plates 55, 55', and suction disks 56 that are operated by compressed air are fitted to the side plates 55, 55'. The suction disks have the function of fixing the driving device 5 to the surface of the structural member. The motors 53, 53' for driving the X- and Y-axes are connected to a locating controller 57, which is in turn controlled by a measurement control system 58.

In FIG. 5, the flaw detection head 40 employs the arrangement of the power feed terminal pairs 2 and the measurement terminals 4 such as shown in later-appearing FIG. 9, for example. The direction of occurrence of a crack is substantially determined depending upon the material of the structural member. Therefore, the power feed terminal pairs 2 and the measurement terminals 4 are disposed in parallel with the crack and are scanned in the directions of the X- and Y-axes 51, 52 in order to measure the potential distribution on the surface of the member on which the driving device 5 can move. If no crack exists, no potential difference occurs between the measurement terminals 2. In the proximity of the crack, the potential difference occurs. If the surface is minutely scanned from the beginning, the measurement time becomes extended. Therefore, the flaw detection head 40 is roughly scanned at first by increasing the measurement gaps to determine rough potential distribution and to determine the occurrence position of the crack. Next, only the portions near the crack occurrence position are finely scanned in order to obtain a detailed potential distribution and to determine the crack shape. The gap for rough measurement at the first stage may be 10 mm or more as can be seen from FIG. 2.

Figure 6:
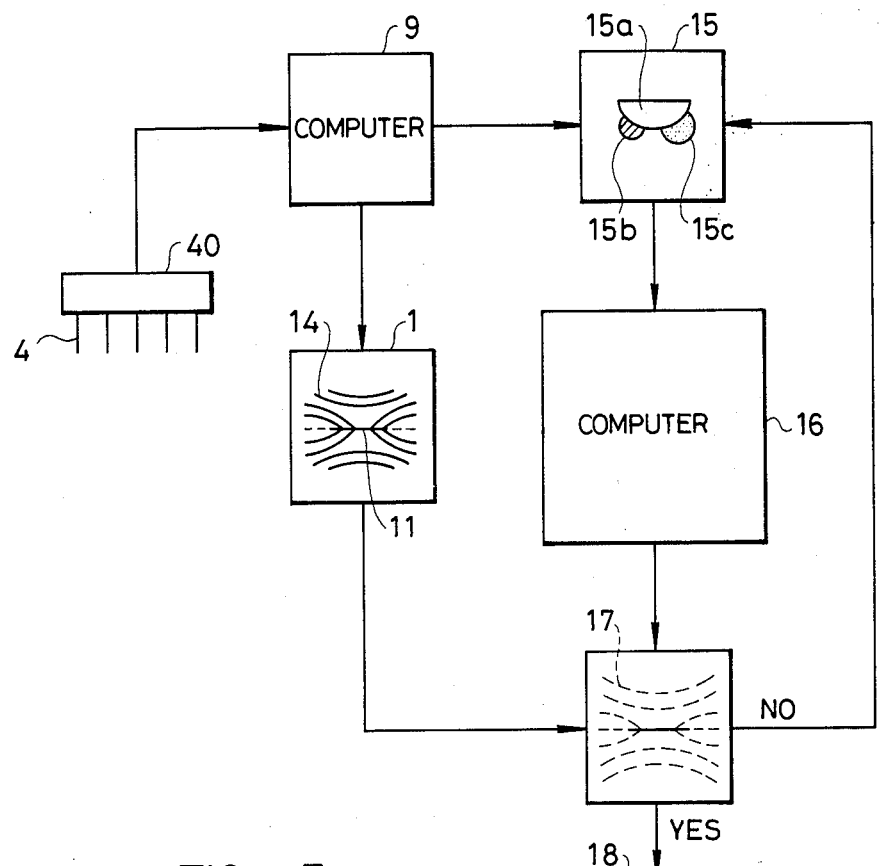
FIG. 6 is a flowchart useful for explaining definitely the method of determining the surface crack shape by the potential distribution obtained from the actually measured values and by the analysis of actually measured values.

FIG. 6 is an explanatory view useful for explaining in further detail the method of detecting the crack shape. The d.c. current is caused to flow through the structural member 1 having the crack 11, and the potential distribution 14 on its surface is measured by scanning the measurement terminals 4 and is inputted to the computer 9. The input potential distribution is compared with the master curve 17 and calculated by the computer 9 to determine the fundamental crack shape 15a. Numeric analysis such as a finite element method is made by the computer 16 using this shape 15a in order to obtain the potential distribution 17. This is then compared with the potential distribution 14 that is measured actually, and corrections such as 15b and 15c are applied to the crack shape so that both potential distributions are equal to each other. The potential distribution is again obtained by calculation. This process is repeated, and the crack 18 obtained when the measured potential distribution 14 and the potential distribution 17 obtained by calculation are in agreement is determined as the surface crack shape. According to this method, the crack shape can be detected highly accurately even if the crack shape is complicated.

If the crack shape is simple, the crack shape can be determined by combining a plurality of master curves.

FIGS. 7 through 12 show various examples of the arrangement of the power feed terminal pairs and the measurement terminals.

Figure 7:
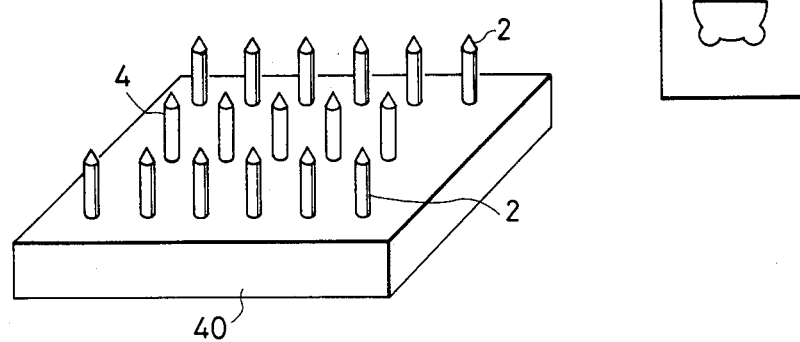
FIG. 7 is a structural view of a flow detection head consisting of power feed terminal pairs and potential measurement terminals.

As shown in FIG. 7, the power feed terminal pairs 2 and the measurement terminals 4 are fitted to the flaw detection head 40, which is a non-conductor substrate, and the measurement terminals 4 are disposed at the center of the power feed terminal pairs 2. If no crack exists on the surface of the structural member, the measurement terminals 4 are on the equipotential line so that no potential difference occurs between them. If any crack exists as shown in FIG. 2, however, the potential difference occurs between them due to the disturbance of the electric field. FIGS. 8 through 12 show the examples of the terminal arrangement for detecting this disturbance of the electric field.

Figure 8:
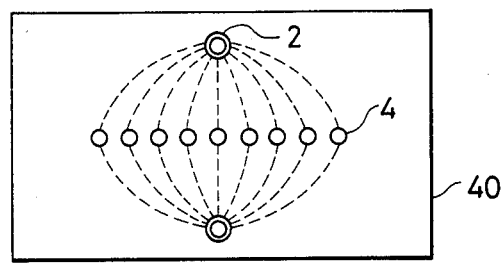
FIG. 8 is a plan view showing the disposition of the power feed terminal pairs and the potential measurement terminals.

In FIG. 8, a plurality of measurement terminals 4 are shown disposed at the center of one power feed terminal pair 2.

Figure 9:
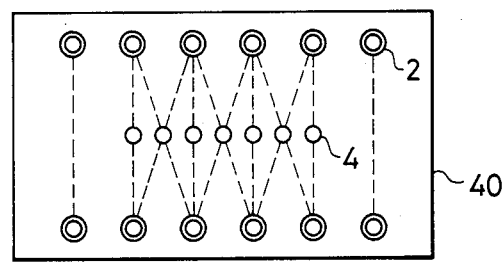
FIG. 9 is a plan view showing another arrangement of the terminals.

In FIG. 9, a plurality of power feed terminal pairs 2 are disposed equidistantly and the measurement terminals 4 are disposed at the center of the former in order to form a uniform electric field in the measurement region.

Figure 10:
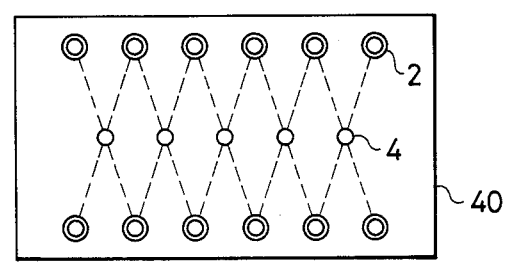
FIG. 10 is a plan view showing still another arrangement of the terminals.

In FIG. 10, the measurement terminals 4 are disposed at the center of the power feed terminal pairs 2 and also at the center of the adjacent power feed terminal pairs 2 so that current density due to the power feed terminal pairs 2 becomes the same current density.

Figure 11:
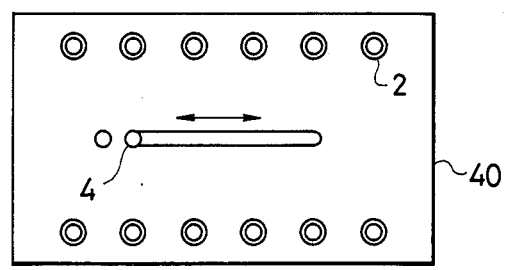
FIG. 11 is a plan view showing still another arrangement of the terminals.

FIG. 11 shows the arrangement wherein two measurement terminals 4 are disposed at the center of the power feed terminal pairs 2 aligned equidistantly, and one of the measurement terminals 4 is fixed with the other movable linearly at the center of the power feed terminal pairs 2, in order to measure the continuous distribution of the potential difference.

Figure 12:
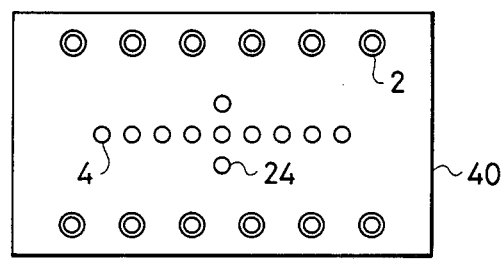
FIG. 12 is a plan view showing still another arrangement of the terminals.

FIG. 12 shows the arrangement wherein two measurement terminals 24 are additionally disposed as the terminals for detecting the crack occurrence position at the center of the measurement terminals 4 of the arrangement shown in FIG. 8 in a direction at right angles to the measurement terminals 4 of the arrangement of FIG. 8.

The arrangements of the power feed terminal pairs 2 and the measurement terminals 4 shown in FIGS. 8 through 12 are for the measurement of the potential distribution parallel to the crack.

Figure 13:
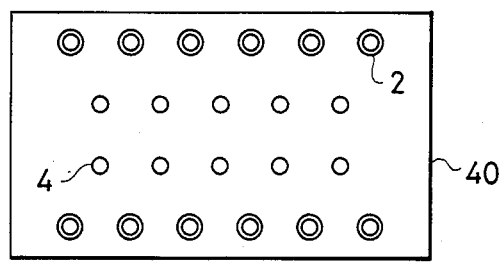
FIG. 13 is a plan view showing still another arrangement of the terminals.

FIG. 13 shows the arrangement wherein the power feed terminal pairs 2 are aligned in parallel with each other with an equidistant gap between the terminals, and the measurement terminal pairs 4 are equidistantly aligned in parallel with each other in such a fashion that the center of the power feed terminal pairs 2 is in agreement with that of the measurement terminal pairs 4 and each of the measurement terminal pairs is positioned at the center between the adjacent power feed terminal pairs 2. This arrangement eliminates the necessity of scanning.

Figure 14:
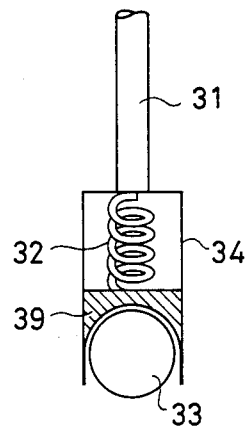
FIG. 14 is a structural view of each of the power feed terminal and the potential measurement terminal.

FIG. 14 shows the electrode structure of the power feed terminal and that of the measurement terminal. (Conventionally, a round rod made of stainless steel or tool steel and having a conical tip has been used as the electrode. Therefore, if the sample to be measured is made of a soft material, it is damaged by the electrode so that the measurement head must be lifted up and moved whenever the measurement position is changed.) This arrangement makes it possible to continuously measure the potential difference distribution while the measurement head is kept pressed to the sample to be measured. A cylinder 34 is disposed at the tip of an electrode rod 31, and a spring 32, a spacer 39 of silver or silver foil and a steel ball 33 are put into the cylinder 34 and are electrically connected to one another. According to this electrode structure, the steel ball 33 is pushed to the surface of the structural member by the spring 32 through the silver spacer 39 and rotates with the movement of the electrode. Therefore, when the potential distribution is measured, continuous measurement and reduction of the measurement time can be accomplished.

Figure 15:
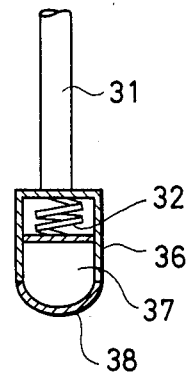
FIG. 15 is a structural view of another arrangement of each terminal.

FIG. 15 shows another embodiment of the electrode. A cylinder 36 having one of the ends thereof sealed is fitted to the tip of the electrode rod 31, and a silver film 38 is bonded to the other open end. The interior of the cylinder 31 is divided into two portions, and a liquid-like material 37 is placed inside the silver film 38 while the spring 39 is placed into the other. According to this construction, the silver film 38 undergoes deformation in accordance with the surface condition of the structural member and reliable contact can be insured.

Figure 16:
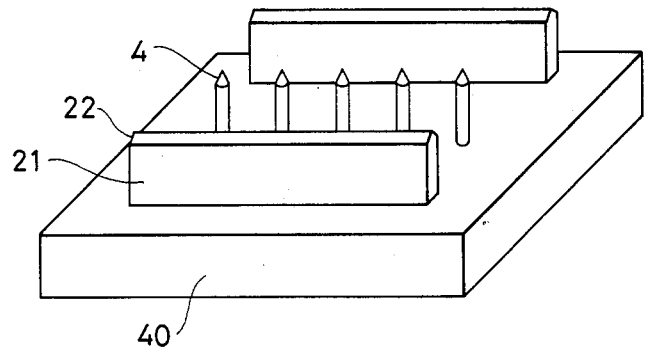
FIG. 16 is a structural view of the power feed terminal.

FIG. 16 shows another embodiment which uses a silver flat plate 22 as the power feed terminal 21. Since silver of a sufficiently small specific resistivity is used as the electrode material, a parallel electric field region can be secured between these electrodes.

Figure 17:
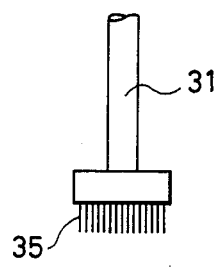
FIG. 17 is a structural view of another arrangement of the power feed terminal.

FIG. 17 shows the arrangement wherein a silver brush 35 is disposed at the tip of the power feed terminal 31. When such a power feed terminal is used, the contact area can be increased by the brush and the contact resistance of the power feed terminal can be reduced by silver having a small specific resistivity.

Figure 18:
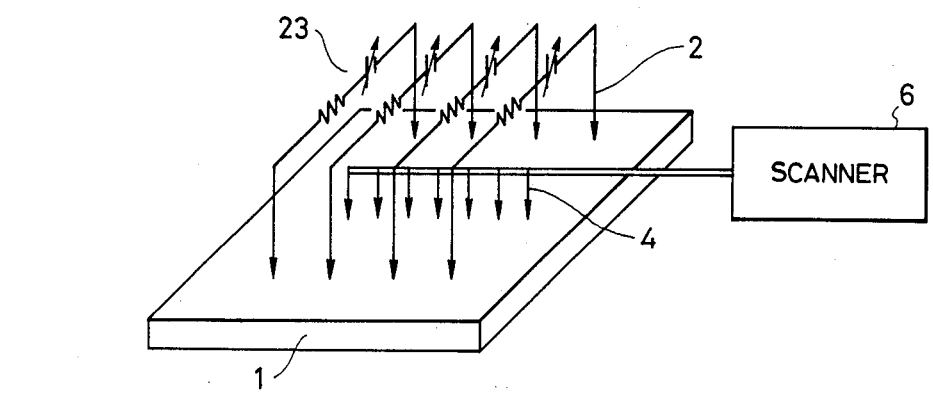
FIG. 18 is a schematic view of the apparatus having an independent constant current source for each power feed terminal in accordance with another embodiment of the invention.

FIG. 18 shows a control system wherein independent constant current sources 23 are disposed for a plurality of power feed terminal pairs 2, respectively, in order to control the current that must be caused to flow through each terminal pair. Since this system can supply a constant current irrespective of the contact state of the power feed terminal pairs 2, a uniform electric field can be generated.

Figure 19:
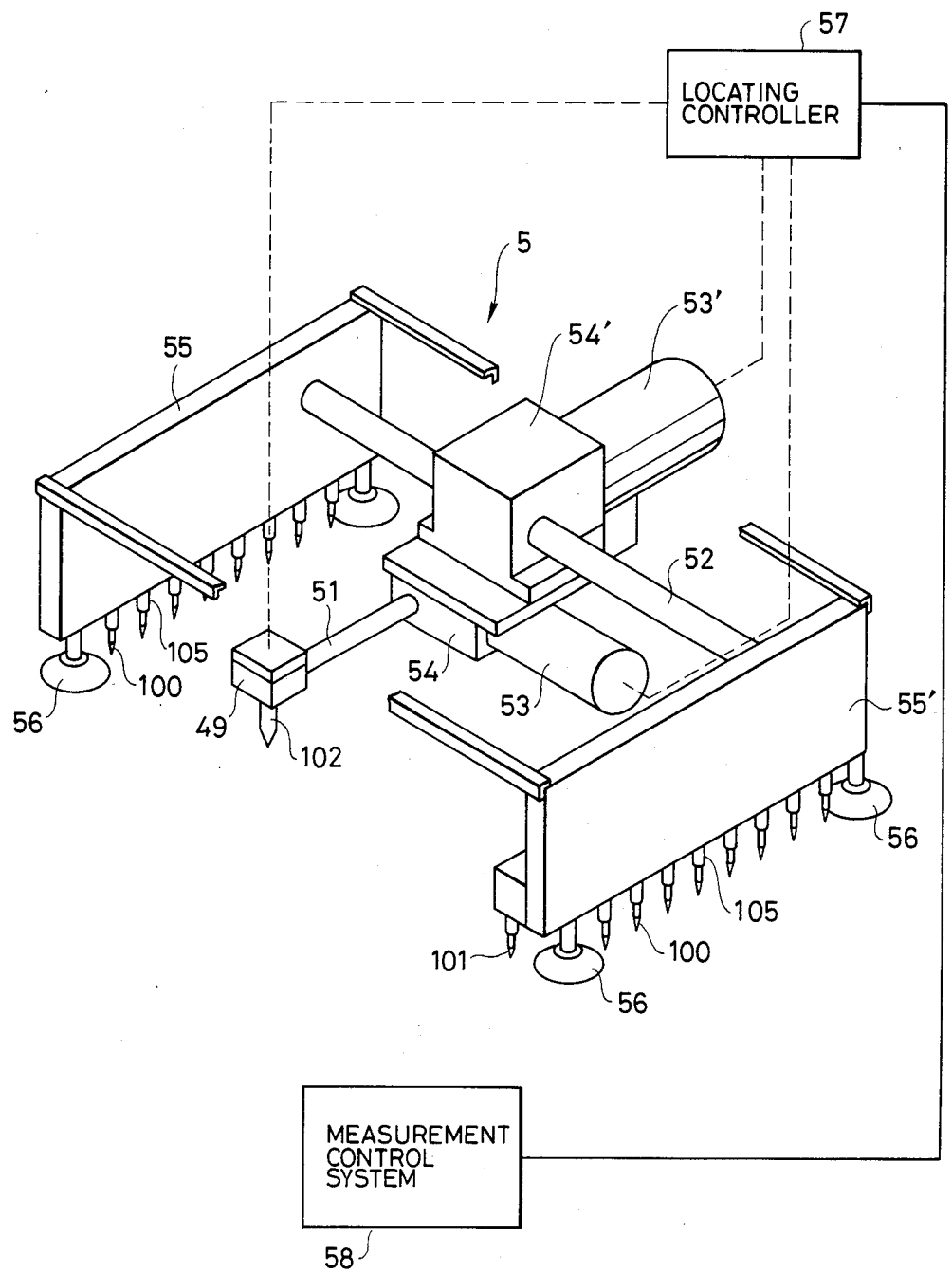
FIG. 19 is a perspective view of the crack shape detection apparatus wherein the power feed terminals are fitted to the side plate of a driving device, in accordance with another embodiment of the invention.

FIG. 19 shows still another embodiment of the crack shape detection apparatus. Unlike the apparatus shown in FIG. 5, the power feed terminals 100 for supplying the d.c. current are not disposed on the flaw detection head in FIG. 19, and the measuring method of the potential distribution is also different. In FIG. 19, a large number of power feed terminals 100 are disposed equidistantly on the side plates 55, 55' of the driving device 5 and each electrode portion is fitted insulatedly to the tip of a cylinder 105 that operates pneumatically. According to this arrangement, the electric field becomes uniform as a whole inside the driving device 5. One (101) of the measurement terminals 101, 102 for measuring the potential distribution is fixed to the side plate 55' with the other (102) being fitted to the flaw detection head 40. Each of these terminals 101, 102 are moved toward the sample to be measured by the pneumatic cylinders. Therefore, the potential distribution can be measured by scanning only one (102) of the measurement terminals. When the measurement terminal 102 is scanned in the direction of the Y axis 52 in this case, the potential difference between it and the fixed measurement terminal 101 increases in proportion to the distance in the direction of the Y axis. Where the crack exists, however, the potential difference becomes greater than that resulting from the proportional relation with the distance ahead of the crack and becomes smaller than that of the proportional relation at the rear of the crack. In this instance, the crack depth is determined from the potential difference between the front and rear portions of the crack.

Figure 20:
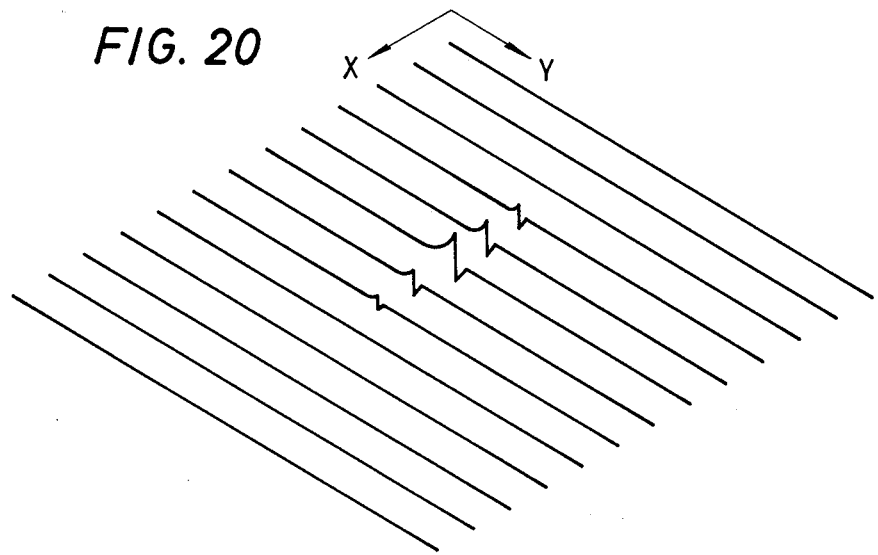
FIG. 20 is schematic view of the potential distribution obtained by scanning the surface of a structural member having cracks.

FIG. 20 shows schematically the potential distribution around the crack which is determined by use of this apparatus. However, the potential distribution is expressed in terms of the deviation from the proportional relation with the distance, that is, the deviation from the reference potential, for ease of illustration. Since disturbance occurs in the potential distribution around the crack, the measurement terminal 102 is first scanned with rough intervals in both X and Y axes directions to detect the crack occurrence position. Then, the potential difference around the crack, particularly the crack at the front and rear of the crack, is measured in order to accurately determine the shape of the crack. Needless to say, if a plurality of measurement terminals 4 are fitted equidistantly to the flaw detection head 40 in place of the single terminal to measure simultaneously the potentials at several positions, the measurement time can be shortened as much. It is also possible to use the construction wherein the measurement terminal 101 fixed to the side plate 55' is not used, two lines of measurement terminals 4 are equidistantly fitted to the flaw detection head 40 and are scanned in the X and Y axes directions to determine the potential difference distribution, and the crack position and the crack shape can thus be detected.

According to the embodiments described above, the flaw detection head having a plurality of power feed terminal pairs for supplying the d.c. current and a plurality of measurement terminals for measuring the potential difference is scanned on the surface of the structural member having the crack and the crack occurrence position can be detected from the change of the potential difference. Next, the d.c. current is applied to the crack in a direction at right angles to the crack direction, and the potential distribution along or across the crack is measured in the proximity of the crack and the crack shape can be accurately detected by use of the master curve prepared in advance from this potential difference. Therefore, the development state of the crack can be obtained accurately.

Figure 21:
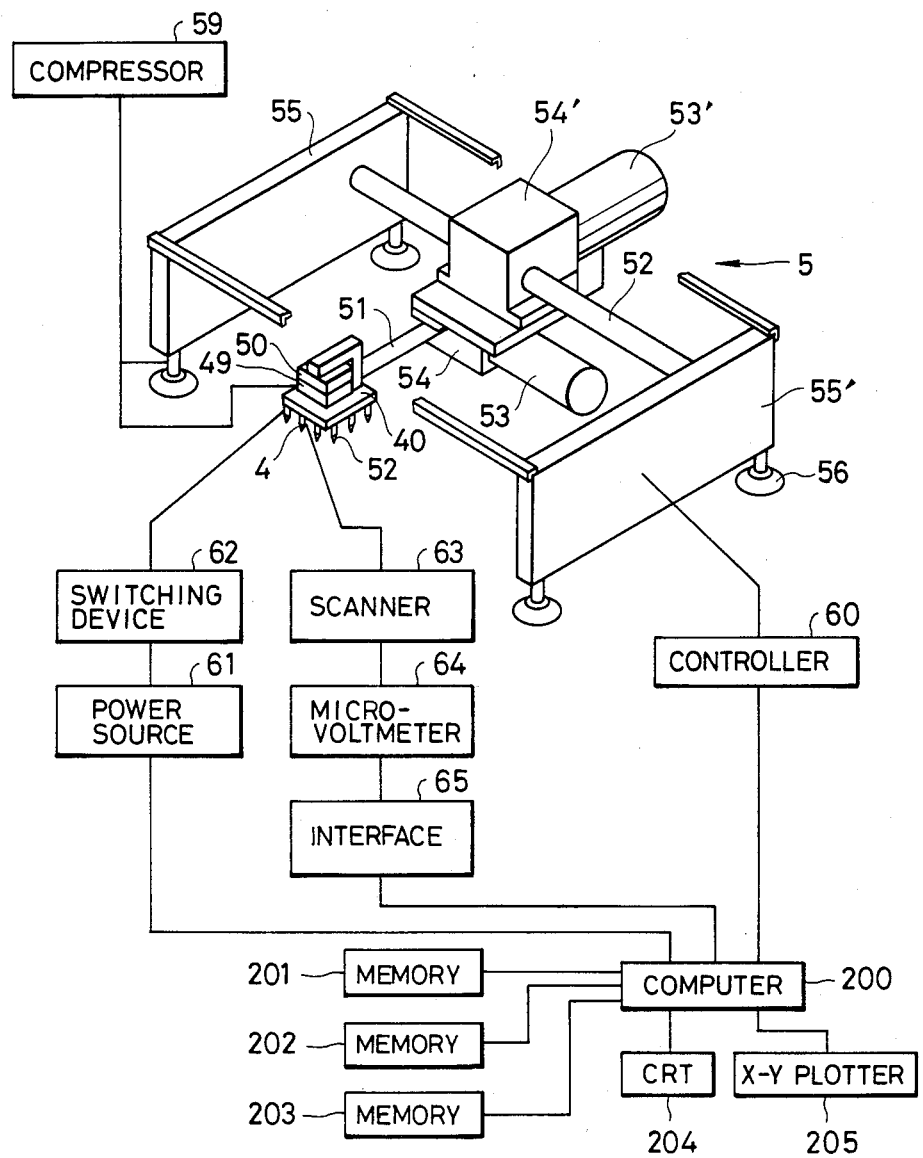
FIG. 21 is a perspective view showing the crack shape detection apparatus in accordance with still another embodiment of the invention.

FIG. 21 shows still another embodiment of the crack shape detection apparatus. Suction plates 56 that operate pneumatically by compressed air supplied from a compressor 59 are fitted to the side plates 55, 55', and have the function of fixing the driving device 5 onto the surface of the structural member. Therefore, it is possible to detect not only a crack on a wall but also on the ceiling. Coordinates driving motors 53, 53' are connected to a driving controller 60, which is in turn controlled by a computer 200.

A d.c. current is applied from a plurality of d.c. power sources 61 to the power feed terminals 2 disposed on the flaw detection head 40 through a switching device 62 in order to generate the electric field on the structural member. The potential differences that occur between a large number of measurement terminals are taken into a micro-voltmeter 64 through a scanner 63 and measured, and is then inputted to the computer 200 through an interface 65. The input data is put together with the position information from a driving device controller 60 and is stored as the potential distribution in a memory 203 connected to the computer 200. The crack position is determined by the computer 200 from the stored potential distribution, and the detailed potential distribution around the crack is measured and comparatively calculated with the potential distribution by analysis of the electric field in order to determine the crack shape.

Figure 22:
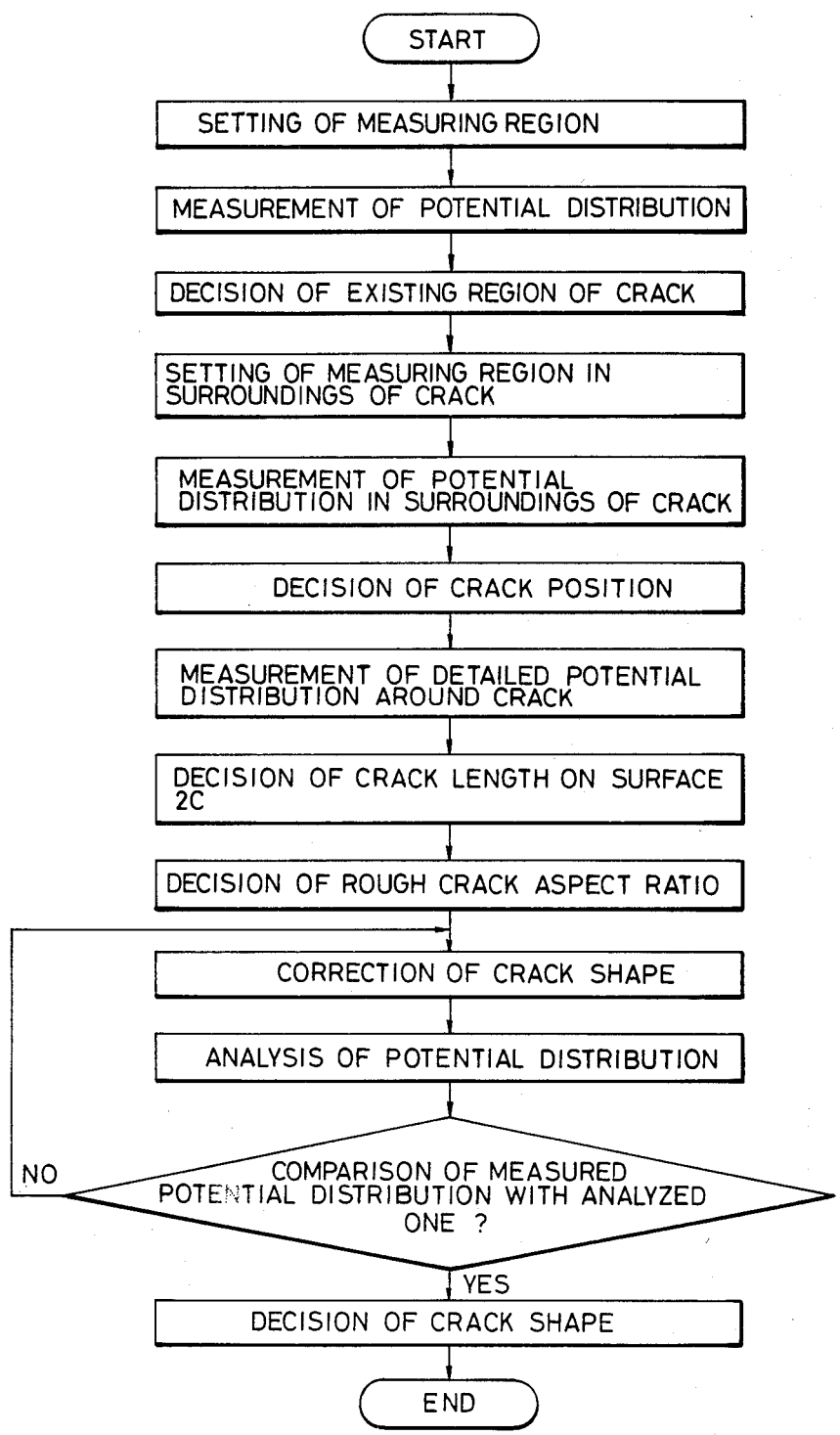
FIG. 22 is a flowchart used for judging the crack shape.

FIG. 22 shows a flowchart for determining the crack shape using a d.c. potential method. First of all, the potential distribution is examined by scanning roughly the flaw detection head 40 throughout the entire region inside the driving device 5 using the driving device shown in FIG. 21. At this time, the crack direction mostly depends upon the material used for the structural member. Therefore, the direction of the flaw detection head 40 is set by stepping motors 53, 53 so that the d.c. current flows in a direction crossing perpendicularly to the crack surface. If any crack exists, the potential distribution such as shown in FIG. 2 occurs so that the crack can be detected easily. Detection can be made sufficiently even at a position spaced apart by 10 mm from the crack, but a shallow crack is unlikely to be detected from time to time. It is safe to make measurement at positions spaced apart by 5 mm from the crack, and hence the measurement gap is sufficiently 10 mm. The rough position of the crack, that is, the existing region of the crack, is thus judged by measuring the potential distribution using this large gap.

Since the potential distributions cause inversion at the front and rear of the crack as shown in FIG. 1, the existence of the crack can be determined to be at this inverting position. Alternatively, when the potential difference distribution is measured across the crack, a greater potential difference than the reference potential difference when the crack does not exist is observed and hence the existence of the crack can be determined to be at such a position. In order to measure accurately the crack shape, the distance of the measuring position from the crack must be set accurately to some extents. Therefore, the potential distribution is measured with a 1 mm gap, for example, within the measuring position where inversion is observed, in order to accurately determine the crack surface. In order to further increase the measuring accuracy, the positions at which the inverted potential distributions become equal are found by finely scanning the flaw detection head 40. In the case of the potential difference measurement, the crack exists at the position at which the potential difference reaches a maximum. Next the potential difference parallel to the crack surface is measured in detail at the positions spaced apart by 1 mm or 2 mm at the front and rear of the crack, or the potential difference distribution across the crack is measured in detail. Here, in the case of the potential distribution the reference potential difference is determined at those positions where no crack exists, and is standardized for the purpose of evaluation. Therefore, the crack shape is determined, after all, in the same way as in the case of the potential difference distribution. For this reason, the following description will deal only with the potential difference distribution.

The crack length 2c on the surface is determined from the detailed potential difference distribution around the crack, and the substantial shape of the crack, that is, an aspect ratio a/c of the crack, is determined from a maximum potential difference ratio $V/V_o$ by the comparative calculation with various master curves stored in the potential difference distribution memory 202 shown in FIG. 21. Next, nodal element data having an aspect ratio which is closest to the aspect ratio estimated from the result of the measurement described above is selected from the nodal point element data of the various aspect ratios stored in a mesh-type memory 201, and are put together with the crack depth estimated from the master curves in order to move and correct the nodal elements at the tip of the crack, and to analyze the potential distribution. The potential difference distribution around the crack is then determined from the potential distribution thus analyzed, and is compared with the result of the measurement. Correction of the crack shape for discordant portions, that is, correction of the nodal elements at the tip of the crack by the discordance, is repeated and finally, the crack shape used for the analysis when it is in agreement with the result of the measurement is determined as the crack shape.

Figure 23:
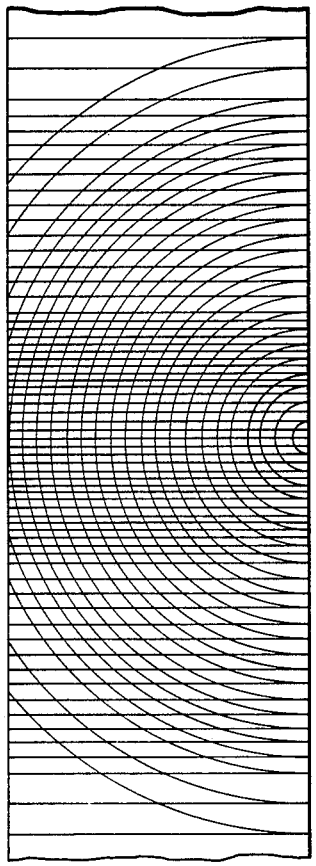
FIG. 23 is a divided view of elements when an aspect ratio is 1.0.
Figure 24:
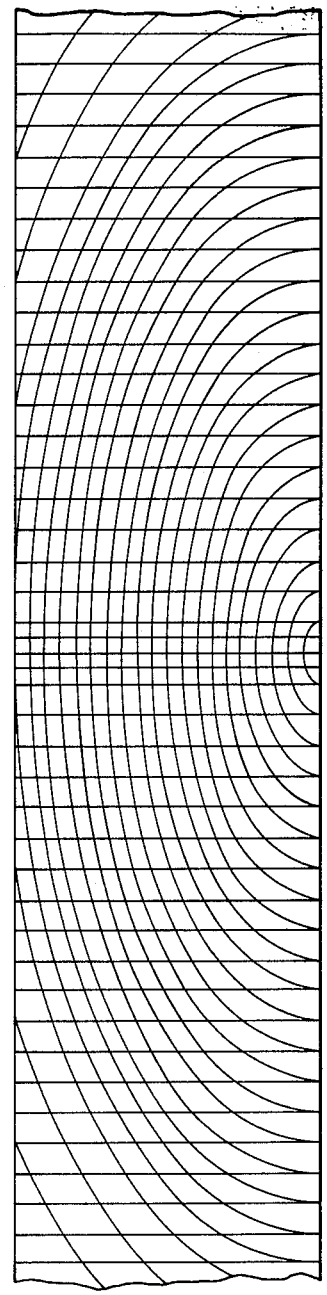
FIG. 24 is a divided view of the elements when the aspect ratio is 0.5.

Hereinafter, crack shape determination shown in FIG. 22 will be described in further detail. Generally, a crack that occurs on the structural member has a shape approximate to a semi-elliptic or semicircular shape. As the nodal elements necessary for the potential distribution of the structural member, semi-circular data such as shown in FIG. 23 is prepared, for example, and the nodal points are moved to match the potential difference distribution measured to form nodal element data having an arbitrary aspect ratio. However, since this is practically troublesome and time-consuming, an element division diagram having an aspect ratio a/c of 0.5, for example, such as shown in FIG. 24 is prepared in advance, and is stored in the memory 201. Then, the nodal element data having an aspect ratio which is most equivalent to the aspect ratio estimated from the result of measurement of the potential distribution is extracted, and is then finely corrected. Such a method is more efficient. The aspect ratios a/c of the nodal element data to be stored in the memory 201 are 1.0, 0.75, 0.5, 0.2 and 0.1, and as the crack depth, the thickness of the structural member is divided every 5% within the range of from 5% to 100% of the thickness.

Figure 25:
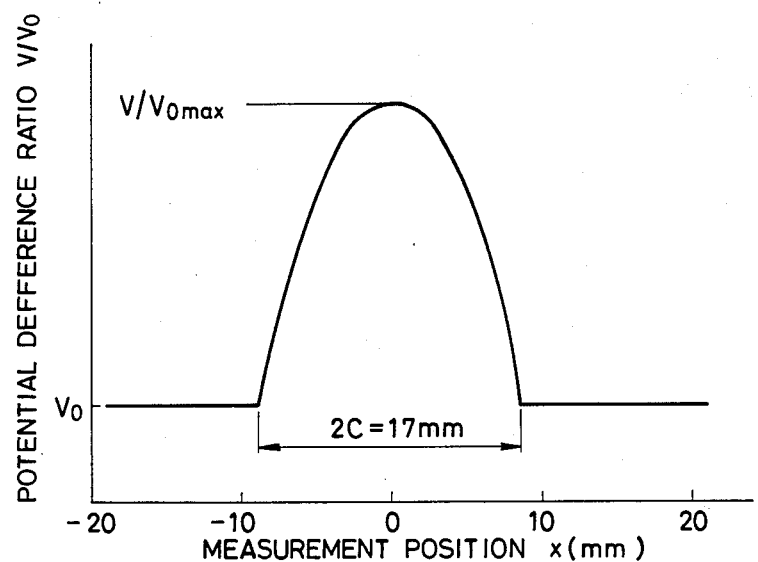
FIG. 25 is a potential difference distribution diagram measured actually around a crack.

A definite method will be explained. FIG. 25 shows a potential difference distribution when the distance between the measurement terminals interposing the surface crack therebetween is set to 5 mm. The abscissa represents the measurement position x mm in the surface direction with the center of the crack being the origin, and the ordinate represents the potential difference ratio V/Vo. Here, symbol Vo represents the potential difference at the position at which no crack exists. As can be seen from FIG. 25, Vo is substantially constant at those portions where no crack exists. Where the crack exists, on the other hand the potential difference becomes great in the same way as in FIG. 2. A peculiar point appears in the potential difference distribution at the tip of the surface crack in the same way as in FIG. 2 and hence the crack length 2c on the surface can be determined easily.

Next, the aspect ratio a/c of the crack is estimated. The position at which the potential difference ratio reaches the maximum corresponds to the deepest point of the crack. Here, the potential difference ratio of the deepest point is supposed to be V/Vo max. The memory 202 for storing the potential difference distribution, shown in FIG. 21, stores therein the center of the crack having various aspect ratios shown in FIG. 26, that is to say, the relation between the potential difference ratio V/Vo at a deepest point and the crack depth a. Here, the crack that is standardized by the thickness t of the structural member to be measured is generally used. For simplicity, it is possible to approximate the relation between the potential difference ratio V/Vo and the crack depth by an n-order equation such as the following equation:

$$V/Vo = 1 + Aa + Ba^2 + Ca^3 + Da^4 + Ea^5$$

Figure 26:
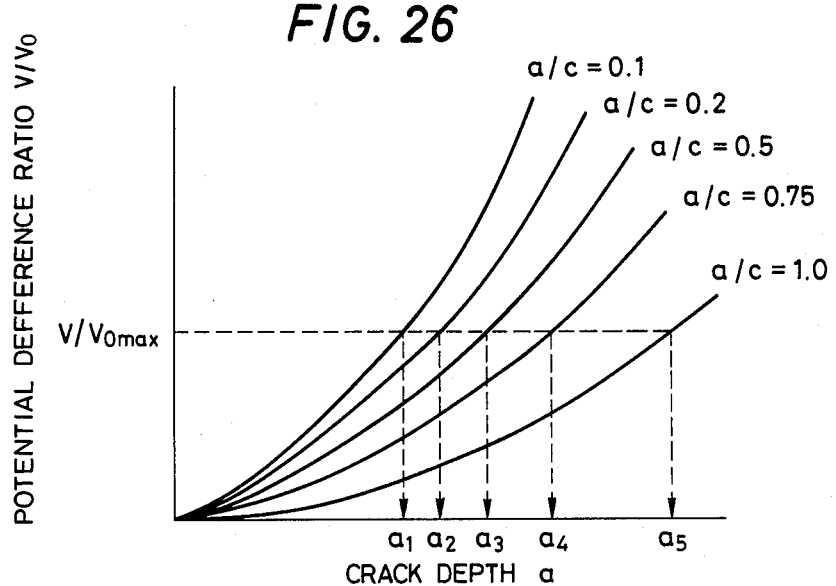
FIG. 26 is a diagram showing the relation between the potential difference and a crack depth.

Next, in conjunction with V/Vo max obtained at the deepest point of the crack, the crack depth is determined by use of the relation between the potential difference ratio V/Vo, which is stored in the memory 201 shown in FIG. 26, and the depth a. In this case, the depth a is found to be $a_1$, $a_2$, $a_3$, $a_4$ and $a_5$ for the aspect ratios a/c of 0.1, 0.2, 0.5, 0.75 and 1.0, respectively. Then, the aspect ratio a/c is determined using the depth $a_1$, $a_2$, $a_3$, $a_4$ and $a_5$ thus obtained, thereby providing $a_1/c$, $a_2/c$, $a_3/c$, $a_4/c$ and $a_5/c$, respectively. Thereafter the ratio of these aspect ratios $a_1/c$ through $a_5/c$ to the aspect ratio a/c of the master curve used is determined, and the aspect ratio of the master curve which is closest to 1 is assumed to be the aspect ratio of the crack because such an aspect ratio is approximate to the actual aspect ratio of the crack. It is hereby assumed that the aspect ratio a/c is 5.

Figure 27:
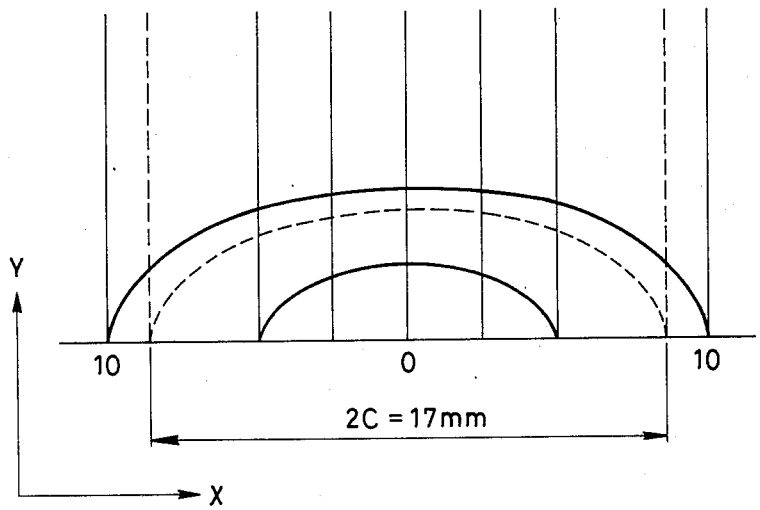
FIGS. 27, 28 and 30 are diagrams showing correction methods of nodal element data.

Next, the potential distribution is calculated. First, nodal element data of the aspect ratio a/c=0.5, which is assumed at first, are called out from the mesh-like memory 201 to the computer 200. The nodal point which is closest to the crack length 2c=17 mm on the surface is selected as shown in FIG. 27. The nodes are set every 5% in the direction of thickness, and the sheet thickness of the member is assumed to be 20 mm. Therefore, the nodes which are closest to the crack length 2c=17 mm on the surface are those which are at the positions spaced apart by ±10 mm from the center of the crack and are 5 mm deep. The nodes which connect the crack tip of 2c=20 mm represented by solid line are moved in both the directions of surface (x direction) and depth (y direction) as represented by dash line so that the solid line is in agreement with the dash line.

Figure 28:
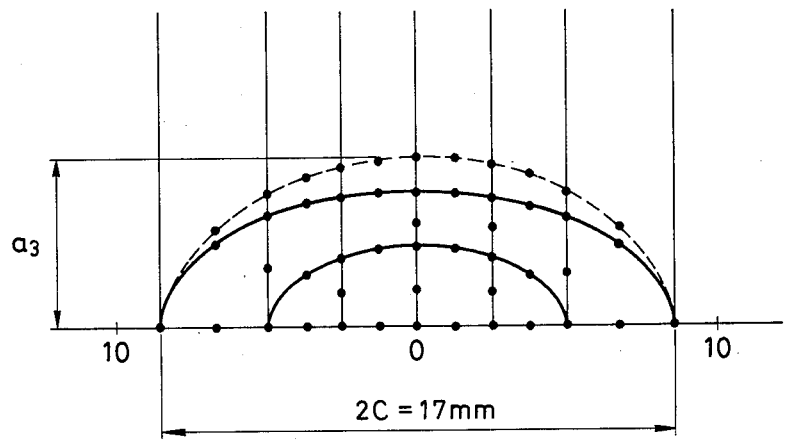

Then, the nodes that are corrected in FIG. 27 are moved so that they are in agreement with the crack depth $a_3$ of the deepest point, which is obtained by use of the master curve of the aspect ratio a/c=0.5 shown in FIG. 26. Here, movement is made in such a manner that the shape of the crack tip becomes semi-elliptical. Then, the electric field is analyzed by the computer 200 by use of the nodal element data corrected as represented by the dash line in FIG. 28.

Figure 29:
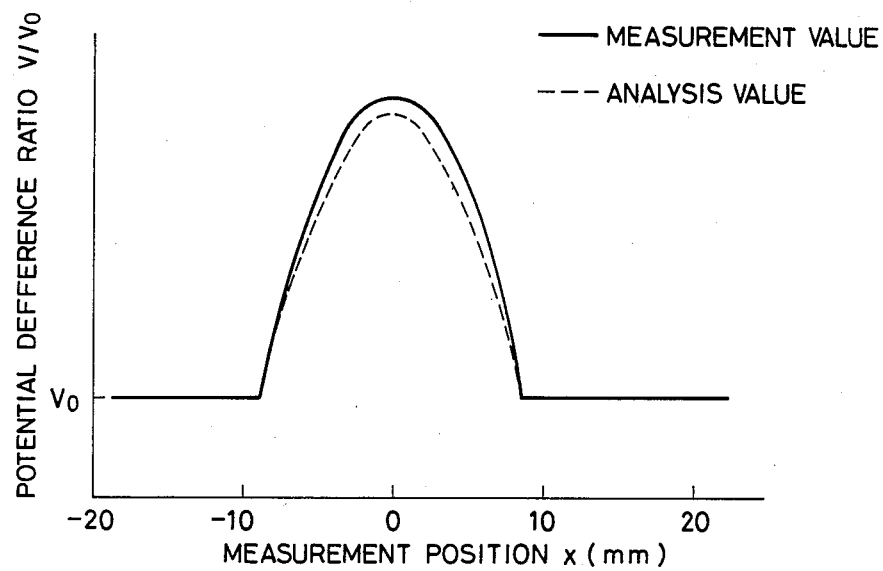
FIG. 29 is a diagram showing comparatively the actually measured value with the analysis value of the potential difference distribution.
Figure 30:
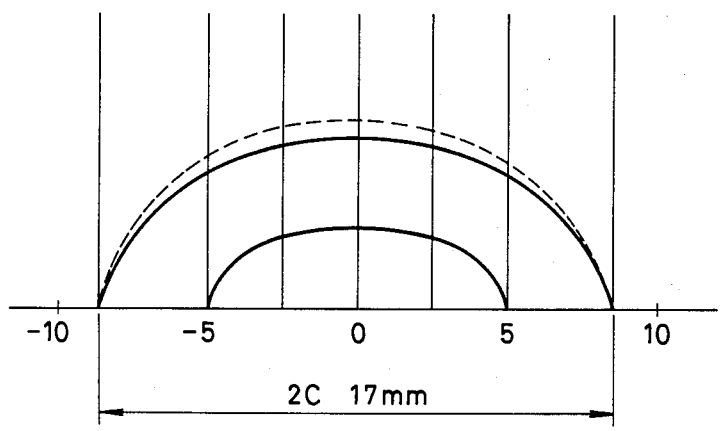

The potential difference distribution around the crack, that corresponds to the actual measurement position, is shown in FIG. 29 on the basis of the potential distribution analyzed in the manner described above. If there is any difference with the measured value represented by the solid line, the node coordinates of the crack tip are moved in the direction of thickness in proportion to the ratio of the potential difference ratio which is measured to the potential difference ratio which is analyzed. This is shown in FIG. 30. In this diagram, the second solid line from the surface represents the crack tip when the analysis is made, and dash line represents the crack tip corrected in proportion to the ratio of the measured value to the analyzed value.

Next, the electric field is analyzed using again the nodal element data represented by the dash line in FIG. 30 by the computer 200 and is compared with the actual measured value. Correction movements of the node at the crack tip is made until they are in agreement with each other. When they are in agreement, the crack shape used for the analysis is judged as the actual crack shape. According to this method, the crack shape can be determined with accuracy of about ±0.1 mm. Needless to say, the potential difference distribution around the crack must be measured accurately for this purpose, but generally it is sufficient to make measurement several times and to obtain the mean value by use of a micro-voltmeter having resolution of about 1 μV. In FIGS. 27 through 30, the nodal elements stored in the mesh-type memory 201 are moved for correction, but the electric field may be analyzed by adding new nodal elements represented by dash line in FIG. 27.

Figure 31:
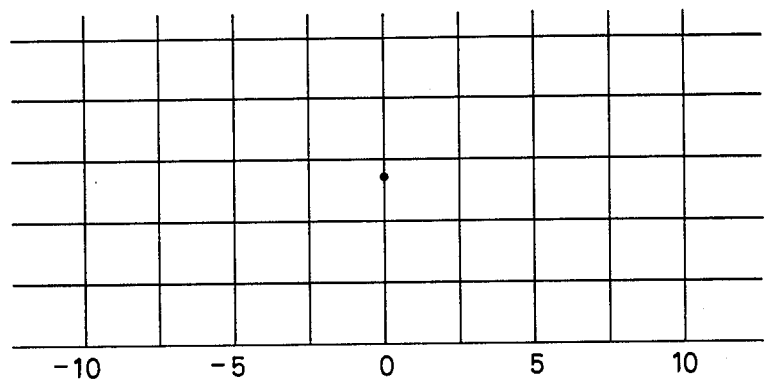
FIG. 31 is a diagram when an element is divided into rectangular segments.
Figure 32:
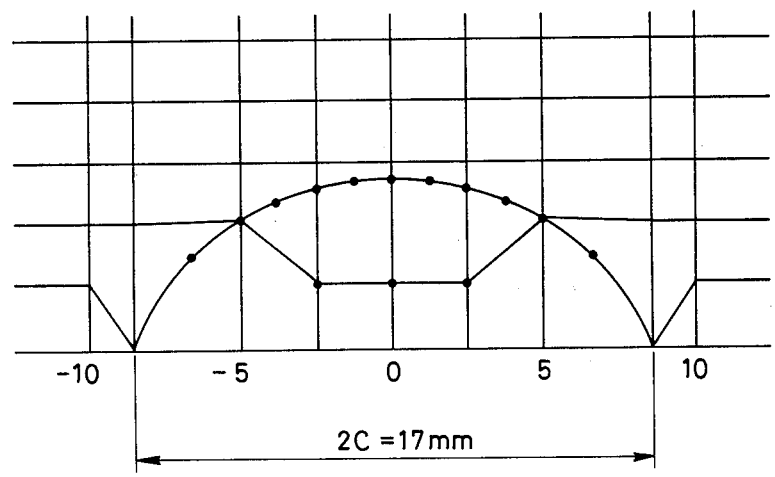
FIGS. 32 and 33 are diagrams showing the correction method of nodal element data.

FIGS. 31 and so on show still another embodiment of the invention. FIG. 31 shows the case where the elements are rectangular. The method using the rectangular elements will now be described. Suppose the potential difference distribution such as shown in FIG. 25 is obtained from the structural member, then, the nodes called out from the mesh-type memory 201 are moved as shown in FIG. 32. In other words, the node closest to the crack length $2c=17$ mm on the surface is selected in the same way as in FIGS. 26 and 27. In FIG. 32, the node gap in the x direction is 2.5 mm, and hence the nodes from 7.5 mm from the crack center are closest to the crack. Therefore, the coordinates of that node in the x direction are moved together with the node in the direction of depth until the equation $c=8.5$ mm is satisfied.

Next, as shown in FIG. 26, the ratios of among the crack depth $a_1$ through $a_5$, which are obtained by use of the master curves of the relation between the potential difference ratios $V/V_o$ for various aspect ratios and the crack depth a, to the crack length $c=8.5$ mm, the crack depth which is obtained by use of the master curve most approximate to the aspect ratio a/c of the master curves used, such as $a_3$, for example, is obtained. The node of $x=0$ mm (on the Y axis) closest to $a_3$ is assumed to be the crack's deepest point. This node is moved in such a manner that it is in conformity with the crack depth $a_3$ and the crack shape is semi-elliptic, for example, within the range from the tip of the crack surface on the surface till the deepest point.

Though shown two-dimensionally in FIGS. 27, 28, 30, 32 and 33, the nodal elements are three-dimensional elements that exist in practice in a direction perpendicular to the crack surface, too. Since the crack shape is curved, the number of nodes constituting the element includes intermediate nodes as 21 node elements so that a curve approximate to the crack shape can be obtained. However, when the rectangular elements are used as in FIG. 32, the nodes and the intermediate nodes must coincide unlike the elliptic elements described above.

Figure 33:
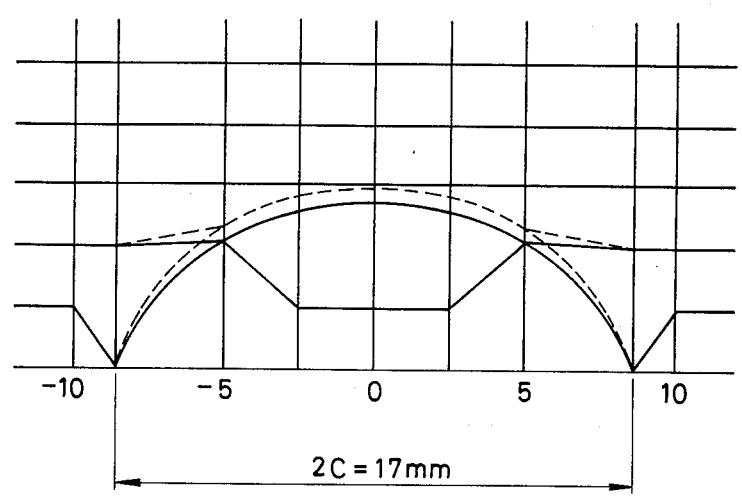

The potential distribution around the crack, and eventually the potential difference distribution, can be obtained by analyzing the electric field by the computer 200 using the nodal element data shown in FIG. 32 and assuming that the potential on the crack surface is zero. If the result turns out such as shown in FIG. 29, the node coordinates of the crack tip represented by the solid line in FIG. 33 is moved in the direction of depth to the shape represented by the dash line by a proportion of the potential difference ratio measured on the structural member in the same way as in FIG. 30 to the potential difference ratio that is analyzed. The electric field is analyzed for the elements of this new crack shape and is again compared with the actual measurement value. Fine correction of the nodes of the crack tip is repeated until the analysis value is in agreement with the measurement value, and the crack shape used for the analysis at the time of agreement is judged as the actual crack shape. This method can determine the crack shape at substantially the same level of accuracy as that of the method using the nodal element data for the crack shape having various aspect ratios described already, but has the advantage over the latter in that only one set of nodal element data needs be stored in the mesh memory 201, the data can be prepared easily because the nodes are regularly arranged, and the data are actually prepared by the natural increment.

Figure 34:
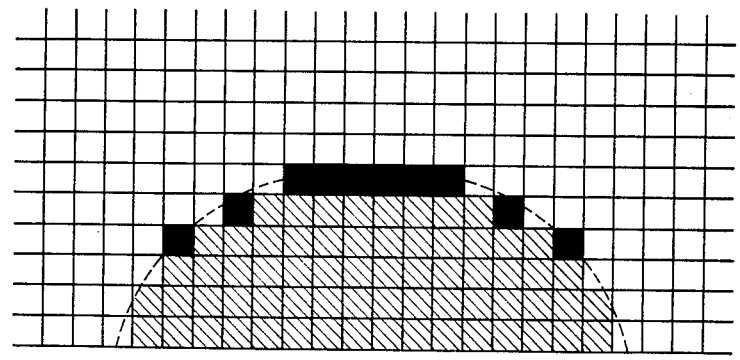
FIG. 34 is a diagram showing a method of judging the crack shape by use of rectangular elements without moving nodal points.

FIG. 34 shows still another embodiment. It is troublesome and time-consuming to prepare in advance elliptic nodal element data or rectrangular nodal element data and to change the nodal data so that they are in agreement with the crack shape. The following is a simple method which determines substantially the crack shape without changing the nodal data. First of all, the portion around the crack of the structural member is particularly divided into fine elements as shown in FIG. 34. In the drawing element having each side of 1 mm is used. If the result of measurement such as shown in FIG. 25 is obtained, the crack length on the surface is $2c=17$ mm. Next, it is assumed that the crack is symmetric and $c=8$ mm. If $a_3$ is obtained by the method shown in FIG. 26, the electric field is calculated by regarding those elements, as the crack surface, which are inside the semi-ellipse as the semi-elliptic crack whose minor axis is $a_3$ and corresponds to the depth of the deepest point and whose major axis is c and corresponds to the surface length. In other words, in FIG. 34, the potential distribution is calculated by regarding the elements with leftward hatchings as the crack surface, that is, by regarding the potential as zero, and if any difference exists such as shown in FIG. 29, the black elements are further added to the crack surface to analyze the electric field. Then, the potential difference distribution is compared with the measurement values, and the elements which are in best agreement are judged as the crack shape. Though the final crack shape shown in FIGS. 30 and 33 is represented by the dash lines in FIG. 33, it can be understood that the crack shape obtained by such a method has also high accuracy.

What is claimed is:

1. A method of detecting the shape of a crack using a scanning measurement terminal means for measuring a potential difference distribution generated between power feed terminal pairs which apply a d.c. current to a surface of a structural member, a control means for driving said scanning measurement terminal means and electric field analysis means for analyzing an electric field, said method comprising the steps of:

storing various aspect ratios of semi-elliptical shapes in a memory circuit of said electric field analysis means;

calculating potential distributions for various crack depths and storing said potential distributions in said memory circuit;

measuring a potential difference distribution of a crack in said surface of said structural member;

selecting an aspect ratio of a calculated potential distribution which is most analogous to said measured potential difference distribution;

altering said selected aspect ratio by moving nodal elements of said selected aspect ratio based on a ratio of said measured potential difference distribution to said calculated potential distribution and obtaining an analyzed potential difference distribution;

repeating the above steps until said analyzed potential difference distribution is equal to said measured potential difference distribution, such that when said analyzed potential difference distribution is equal to said measured potential difference distribution, the shape of the crack is represented by the corresponding altered aspect ratio.

2. A method of detecting the shape of a crack according to claim 1, wherein said various aspect ratios analysis means are 1.0, 0.075, 0.5, 0.2 and 0.1, respectively, and depths of the crack stored in said memory circuit are 5%, 10%, 15%, 20%, 25%, 30%, 35%, 40%, 45%, 50%, 55%, 60%, 65%, 70%, 75%, 80%, 85%, 90%, 95% and 100% of the thickness of said structural member, respectively.

3. A method of detecting the shape of a crack according to claim 1, further comprising the steps of:

dividing said structural member into a plurality of element using an automatic element division program incorporated in said electric field analysis means by imputting the shape of said structural member into said electric field analysis means; and inputting the crack shape and a current application position to said electric field analysis means to analyze said potential distribution.

* * * * *